(12) United States Patent
Amtmann et al.

(10) Patent No.: US 6,284,798 B1
(45) Date of Patent: Sep. 4, 2001

(54) GUANIDINE DERIVATIVES, METHODS OF PREPARING THEM AND THEIR USE AS DRUGS

(75) Inventors: Eberhard Amtmann; Norbert Frank; Gerhard Sauer, all of Heidelberg; Gerhard Schilling, Ladenburg, all of (DE)

(73) Assignee: Cancer Research Ventures Limited, London (GB)

( * ) Notice: Subject to any disclaimer, the term of this patent is extended or adjusted under 35 U.S.C. 154(b) by 0 days.

(21) Appl. No.: 09/194,321

(22) PCT Filed: May 23, 1997

(86) PCT No.: PCT/EP97/02658

§ 371 Date: Oct. 18, 1999

§ 102(e) Date: Oct. 18, 1999

(87) PCT Pub. No.: WO97/45401

PCT Pub. Date: Dec. 4, 1997

(30) Foreign Application Priority Data

May 24, 1996 (DE) .............................. 196 21 038

(51) Int. Cl.[7] .................. A61K 31/15; A61K 31/155; C07C 279/18
(52) U.S. Cl. ................ 514/632; 514/631; 564/277; 564/227
(58) Field of Search .................. 564/227, 277; 514/632, 631

(56) References Cited

U.S. PATENT DOCUMENTS

| 3,914,308 | 10/1975 | McCoy et al. . |
| 4,709,094 | 11/1987 | Weber et al. . |
| 5,093,525 | 3/1992 | Weber et al. . |

FOREIGN PATENT DOCUMENTS

| 932951 | * 7/1963 | (GB) . |
| 9002398 | 5/1990 | (WO) . |
| 9101447 | 3/1991 | (WO) . |
| 9106030 | 8/1991 | (WO) . |
| 9201050 | 2/1992 | (WO) . |

OTHER PUBLICATIONS

Chemical abstracts vol. 60, 1607 g, Oct. 1960.*
CA:87:23199 abs of Probl. Farm. by Gagauzov et al, 3 , pp 51–6, 1975.*
CA:68:111391 abs of J Mol Biol by Sanchez et al 30 (2) pp 223–53, 1967.*

Z. Jerushalmy, et al. Inhibition by Guanidino Compounds of Platelet Aggregation Induced By Adenosine Diphosphate. *Biochemical Pharmacology* (1966) 15:1791–1803.

Krishna C. Agrawal, et al. Potential Antitumor Agents. II. Effects of Modifications in the Side Chain of 1–Formylisoquinoline Thiosemicarbazone[1,2]. *J. Med. Chem.* (1969) 12,5:771–774.

Barnett S. Pitzele, et al. Potential Antisecretory Antidiarrheals. 1. $\alpha_2$–Adrenergic Aromatic Aminoguanidine Hydrazones. *J. Med. Chem.* (1988) 31:138–144.

Raj Nandan Prasad, et al. Acylation of guanidines and guanylhydrazones. *Canadian Journal of Chemistry*. (1967) 45: 2247–2252.

William O. Foye, et al. Synthesis and Biological Activity of Guanylhydrazones of 2–and 4–Pyridne and 4–Quinoline Carboxaldehydes. *Journal of Pharmaceutical Sciences* (Jun. 1990) 79,6:527–530.

Basil Jason Heywood, et al. Improvements in or relating to Guanidines. Patent Specification No. 932951—The Patent Office—London. Published Jul. 13, 1963.

Chemical Abstracts. (1975) vol. 83, 53182:16.

* cited by examiner

*Primary Examiner*—Jean F. Vollano
(74) *Attorney, Agent, or Firm*—Dann Dorfman Herrell and Skillman, P.C.

(57) ABSTRACT

The invention concerns new guanidine derivatives of formula (I), methods of preparing them and their use in drugs containing compounds, of formula (I), wherein

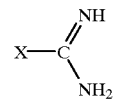

(I)

X is —NH—NH—$CH_2R_1$ and $R_1$ denotes $C_8$ to $C_{20}$ alkyl.

wherein x is —NH—NH—$CH_2R_1$ and $R_1$ denotes $C_8$ to $C_{20}$ alkyl.

6 Claims, 7 Drawing Sheets

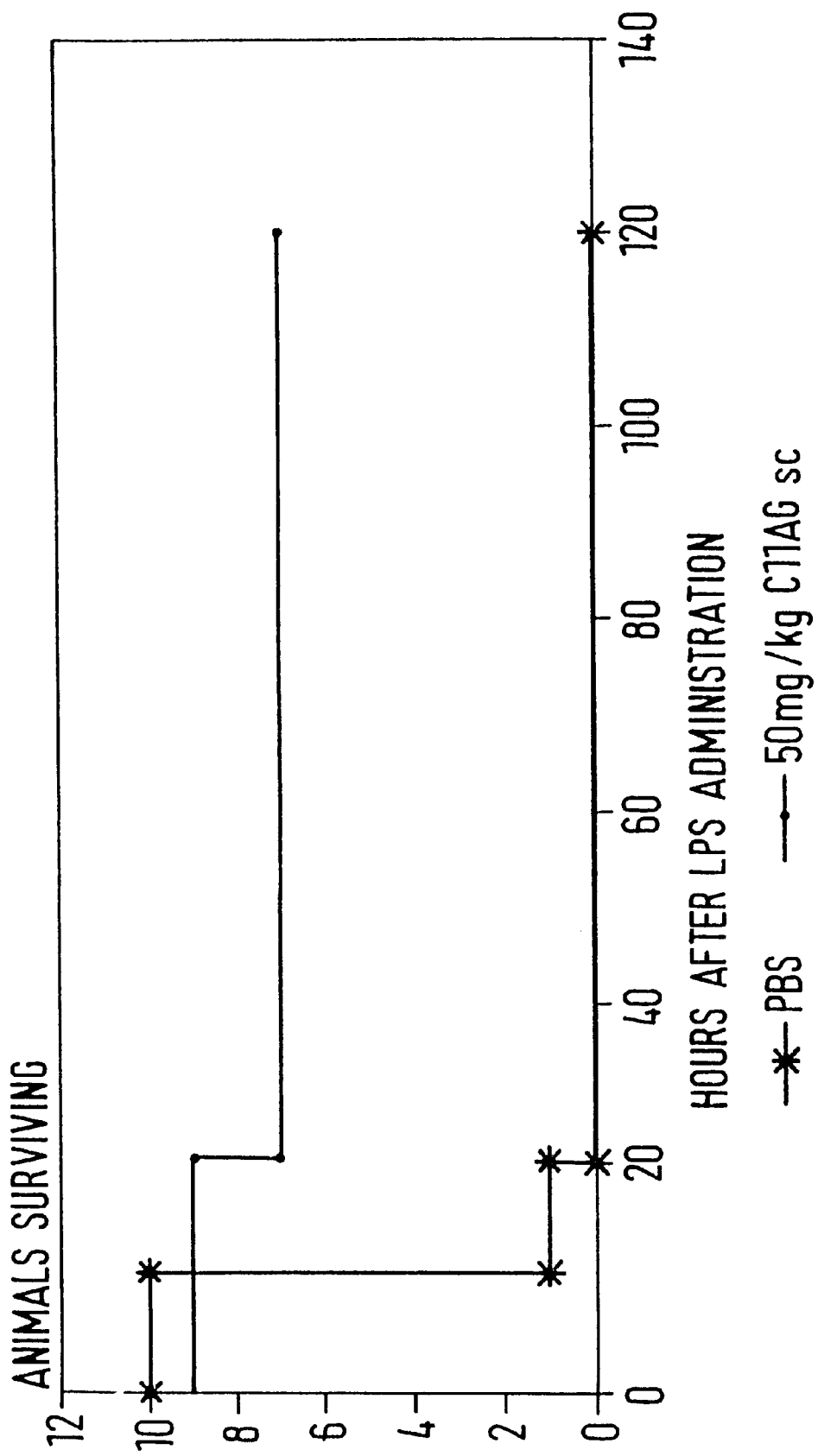

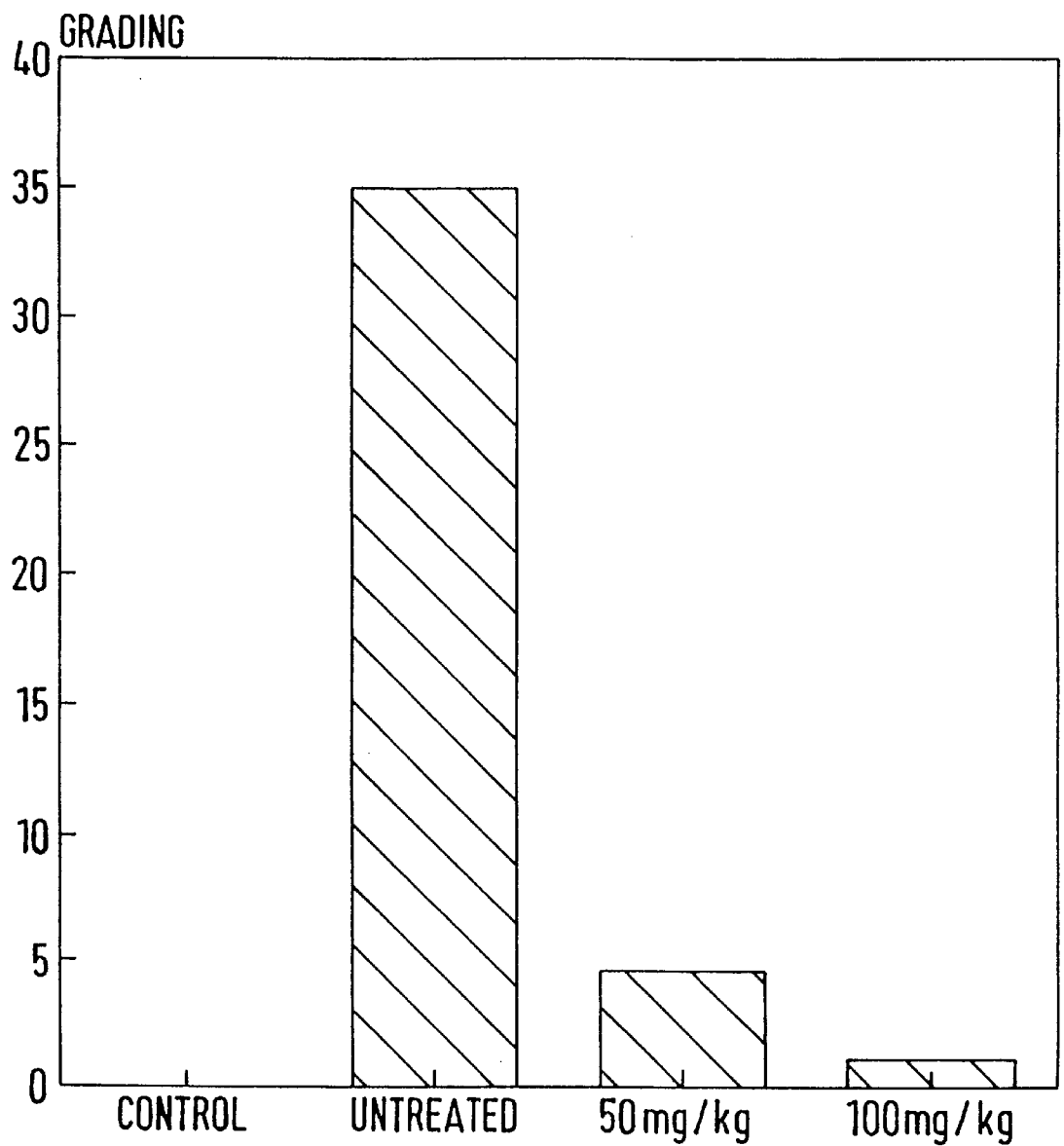

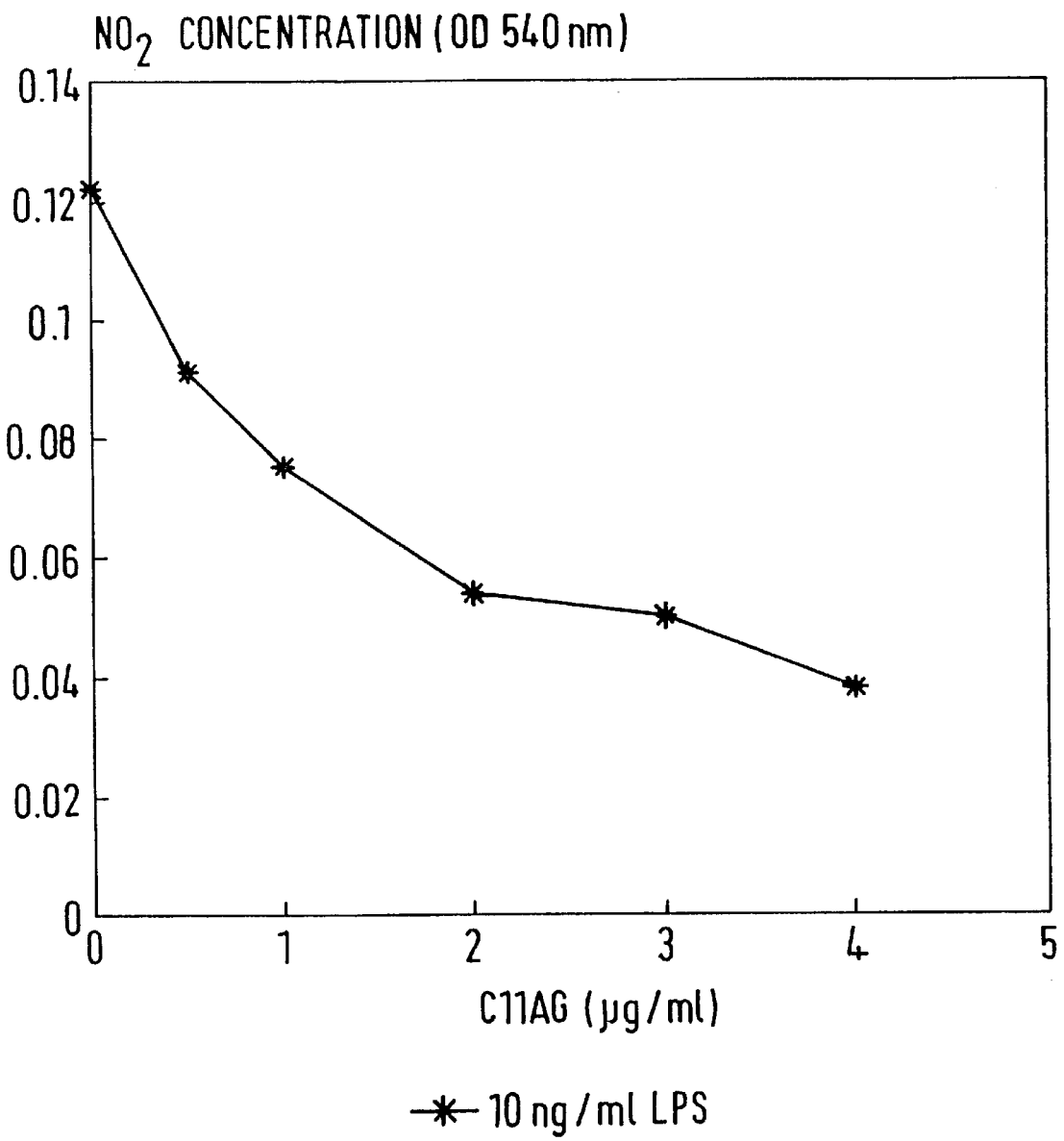

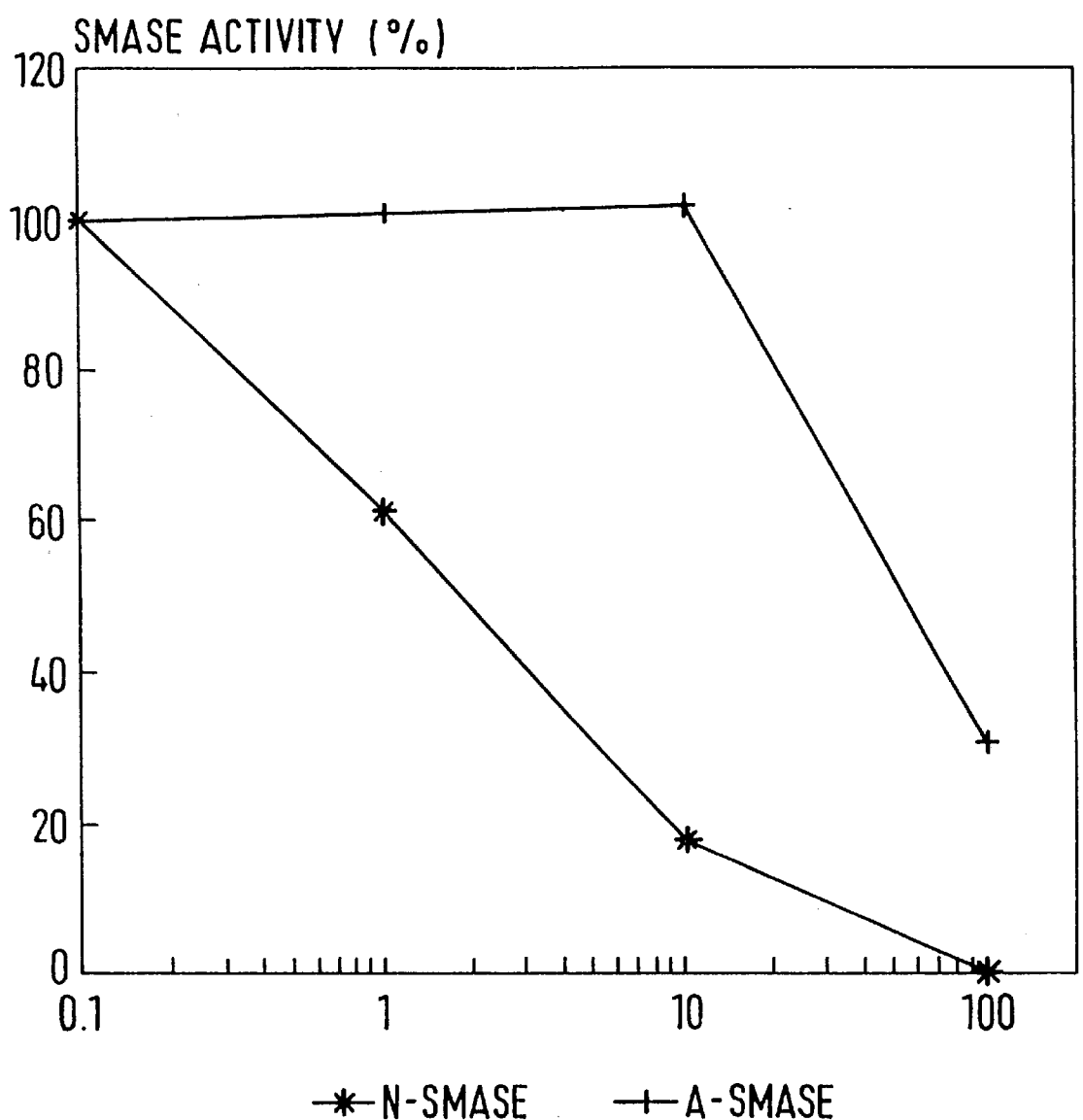

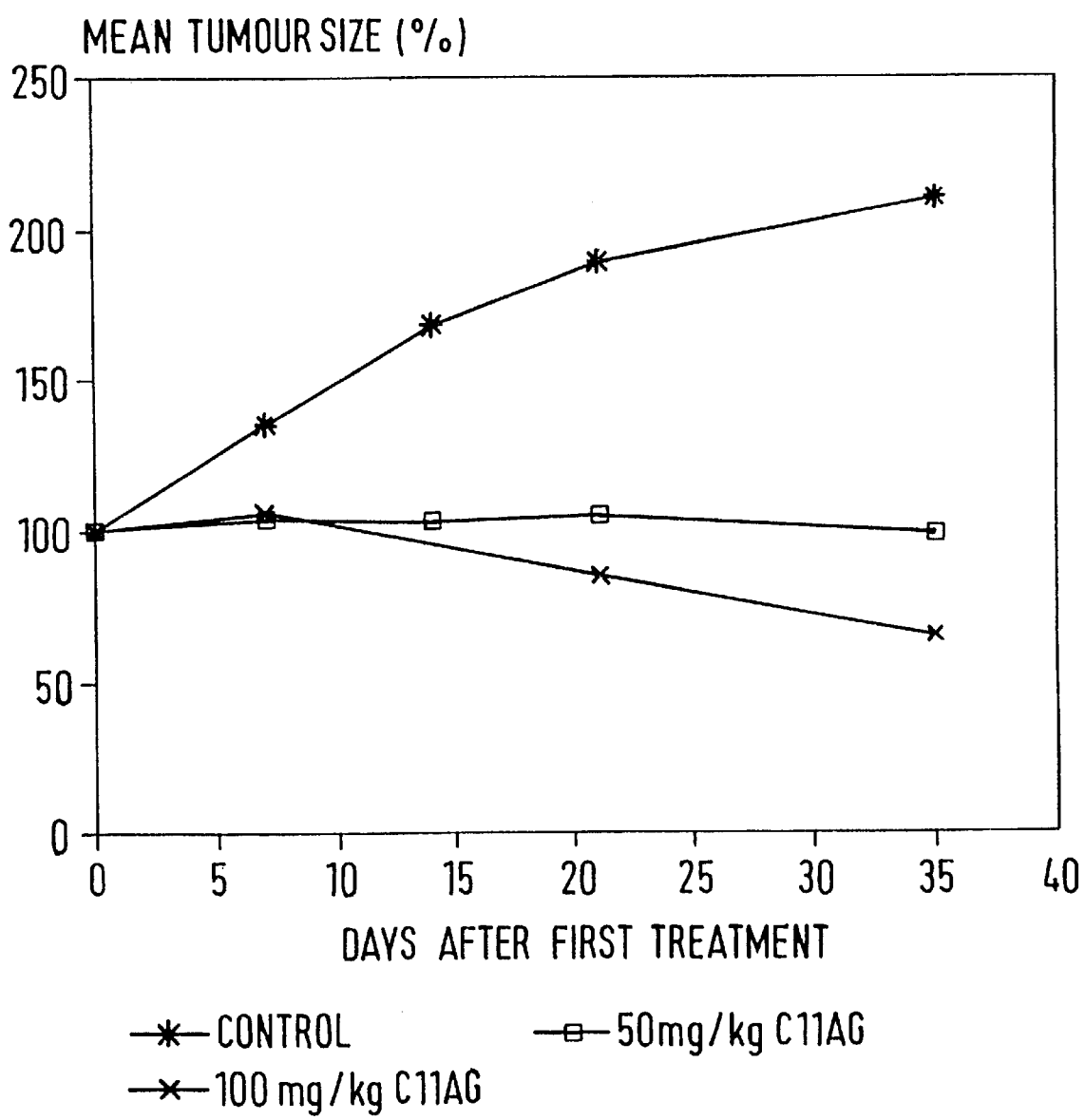

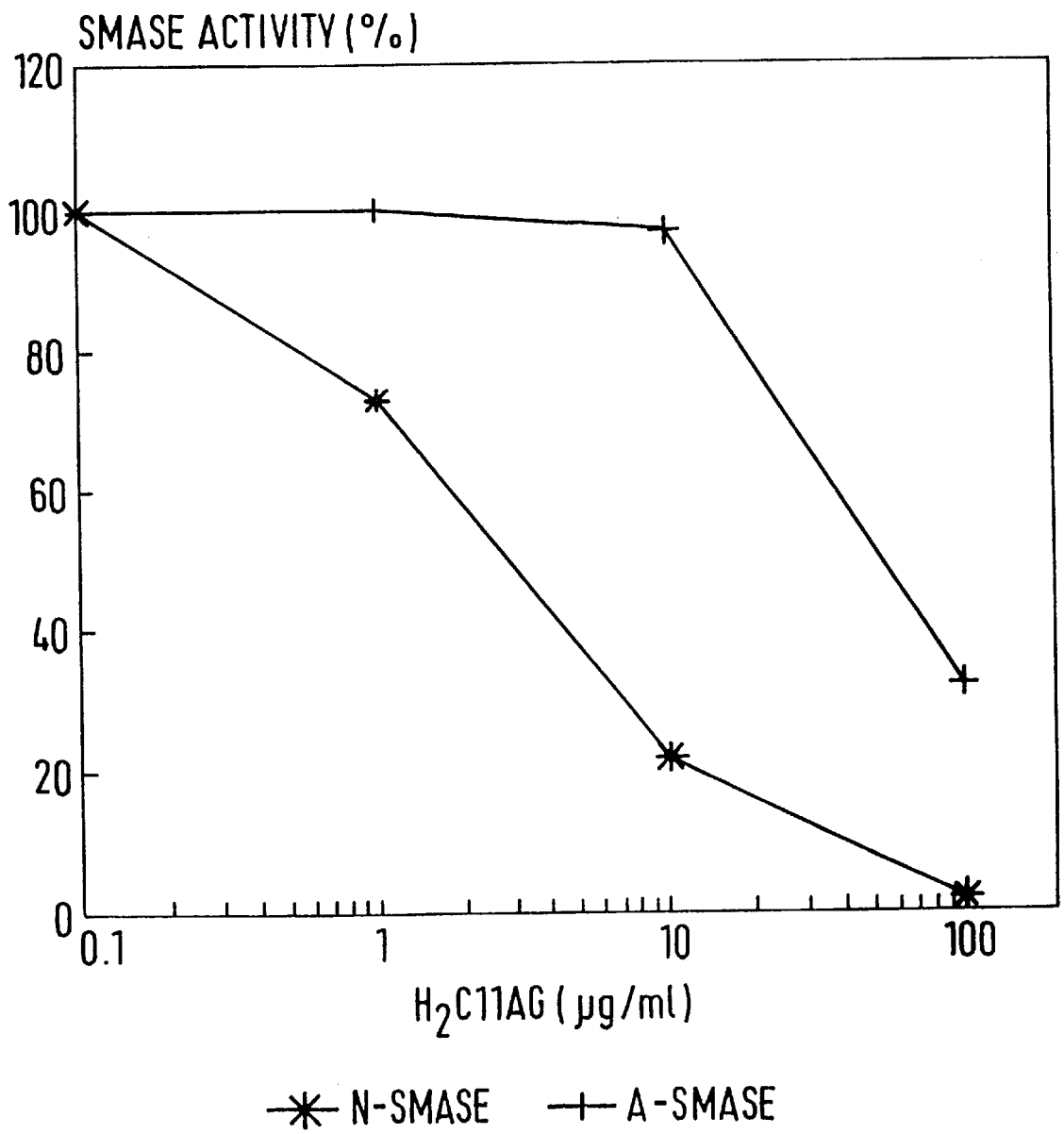

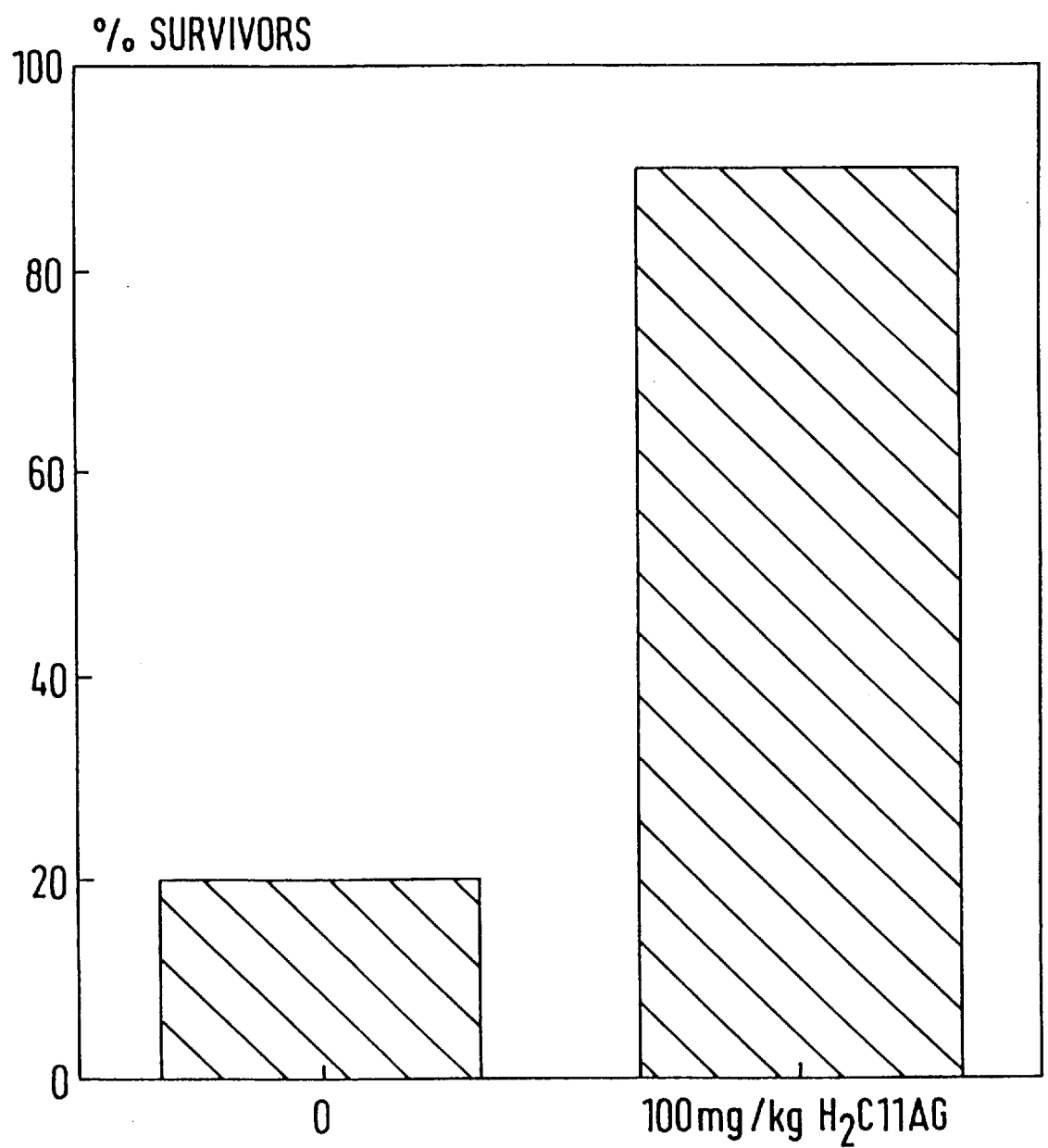

GUANIDINE DERIVATIVES, METHODS OF PREPARING THEM AND THEIR USE AS DRUGS

This is the national phase of PCT/EP97/02658 filed May 23, 1997, now WO 97/45401.

The present invention relates to new guanidine derivatives, processes for preparing them and their use as sphingomyelinase inhibitors and pharmaceutical compositions which contain these compounds. The guanidine derivatives of the present invention correspond to the general formula I:

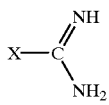

wherein
X denotes $R_1$, —$NHR_1$, —NH—NH—$CHR_1R_2$, —NH—N=$CR_1R_2$,

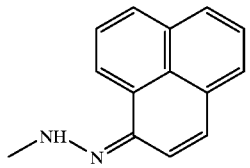

$R_1$ and $R_2$ independently of each other denote hydrogen, a straight-chained or branched $C_{3-20}$-alkyl, $C_{3-20}$-cycloalkyl group, an adamantyl, norbornyl, tricyclodecyl, benzyl, furyl, pyridyl, indolyl, quinolyl, anthracenyl, phenanthryl, perinaphthyl or quinuclidinyl group, wherein the above-mentioned straight-chained or branched $C_{3-20}$-alkyl group may be substituted by a hydroxy or $C_{1-4}$-alkoxy group, a halogen atom or an amino group and the above-mentioned $C_{3-20}$-cycloalkyl group may be substituted by a hydroxy, $C_{1-4}$-alkoxy, $C_{1-4}$-alkyl group or by a halogen atom or an amino group, and wherein, if X denotes —NH—N=$CR_1R_2$, only one of the substituents $R_1$ and $R_2$ may represent hydrogen optionally in the form of individual optical isomers, mixtures of the individual isomers or racemates, tautomers or geometrical isomers e.g. cis/trans-isomers as well as in the form of the free bases or the corresponding acid addition salts with pharmacologically acceptable acids.

Preferred compounds of general formula I are those wherein
X denotes —NH—NH—$CH_2R_1$ and —NH—N=$CHR_1$
$R_1$ denotes $C_{8-20}$-alkyl (branched or unbranched).

Particularly preferred compounds of general formula I are those wherein
X denotes —NH—NH—$CH_2R_1$ and —NH—N=$CHR_1$ and
$R_1$ denotes an unbranched decyl group.

The compounds according to the invention have valuable pharmacodynamic and biochemical properties and can therefore be used advantageously in research and in human and veterinary medicine.

Surprisingly it has been found that the aminoguanidines and amidines according to the invention have beneficial sphingomyelinase-inhibiting, antimicrobial, antiviral, anti-inflammatory (e.g. anti-shock) activities and effects on cell growth.

The compounds according to the invention are prepared by reacting an aldehyde or ketone of formula $R_1CHO$ or $R_1COR_2$ with aminoguanidine. The reaction is usually carried out in an inert organic solvent, e.g. a chlorinated hydrocarbon, such as dichloromethane or chloroform, or an aromatic hydrocarbon such as benzene or toluene. The reaction is preferably carried out by removing the water formed from the equilibrium, e.g. using a water separator. The reaction may be carried out over a wide temperature range but is generally performed at elevated temperature, particularly at a temperature in the range from about 60° C. up to the boiling point of the reaction mixture. In addition, the compounds according to the invention may be prepared by methods known from the prior art.

The starting compounds are known or may be prepared by known methods.

The pharmaceutical compositions according to the invention contain one of the above-mentioned compounds of general formula I in a conventional solid or liquid pharmaceutical carrier. The compounds according to the invention may also be combined with known active substances.

The compounds according to the invention are characterised by anti-inflammatory (e.g. anti-shock), antimicrobial, antitumoral and, in particular, antiviral effects. The antiviral spectrum of activity includes, for example, herpes, vesicular stomatitis, HIV and papilloma viruses. It has also been found that the compounds according to the invention influence the growth of tumour cells. They may be used to treat carcinomas, e.g. carcinoma of the large intestine, sarcomas or leukaemias.

In general, it is found that these substances according to the invention bring about an NF-kappaB-dependent immunosuppression.

The compounds according to the invention can therefore be used to treat the following diseases:

A. Systemic inflammatory reactions
   sepsis-causing diseases
      gram-positive sepsis
      gram-negative sepsis
      fungal sepsis
      agranulocytosis (neutropenic fever)
      urinary infections (urosepsis)
      general infections with meningococci (meningococcaemia)
   trauma/haemorrhage
   burns
   injuries caused by ionising radiation
   acute pancreatitis
   adult respiratory distress syndrome (ARDS)
B. Reperfusion syndrome
   post pump syndrome
   ischaemia-induced reperfusion injury
C. Cardiovascular disease:
   cardiac stun syndrome
   myocardial infarction
   congestive heart failure
   arteriosclerosis
D. Infectious diseases:
   papilloma virus infection
   herpes virus infection
   HIV infection/HIV neuropathy
   meningitis
   hepatitis
   septic arthritis
   peritonitis
   pneumonia bronchitis
epiglottitis
*E. coli* 0157:H7 infection
haemolytic uremic syndrome/thrombolytic thromocytopenic purpura
malaria
Dengue haemorrhagic fever
Leishmaniasis
leprosy
toxic shock syndrome
*Streptococcal myositis*
gas gangrene
myobacterium tuberculosis infections
myobacterium avium intracellular infections
pneumocystosis
pelvic inflammatory disease
orchitis/epidydimitis
Legionella
lyme disease
influenza A virus infection
diseases caused by Epstein-Barr virus
viral-associated haemaphagocytic syndrome
viral encephalitis/aseptic meningitis
E. Gynaecological applications
premature labour
miscarriage
infertility
F. Inflammatory diseases/autoimmune diseases:
rheumatoid arthritis/seronegative arthropathy
emphysema bronchitis (chronic obstructive pulmonary disease COPD)
osteoarthritis
inflammatory bowel disease
Crohn's disease
systemic lupus erythematosis
iridocyclitis/uveitis/optic neuritis
idiopathic pulmonary fibrosis
systemic vasculitis/Wegner's granulomatosis
sarcoidosis
orchitis/vasectomy reversal procedures
H. Allergic/atopic diseases:
asthma
allergic rhinitis
eczema
allergic contact dermatitis
allergic conjunctivitis
hypersensitive pneumonitis
I. Malignant disease:
tumour therapy in combination with chemotherapy, radiotherapy and cytokine treatment such as TNF-α treatment of sarcomas, carcinomas and leukaemias
ALL
AML
CML
CLL
breast cancer
small-cell and non-small-cell bronchial carcinoma
squamous cell carcinoma
Hodgkin's disease, non-Hodgkin's lymphoma
multiple melanoma
Kaposi's sarcoma
colorectal carcinoma
nasopharyneal carcinoma
malignant histiocytosis
paraneoplastic syndrome/hypercalcaemia of malignancy
J. Transplant complications
rejection reactions after transplant
graft versus host reactions
K. Cachexia
L. Congenital diseases:
cystic fibrosis
familial hematophagocytic lymphohistiocytosis
sickle cell anaemia
M. Skin diseases:
psoriasis
alopecia
N. Neurological diseases/chronic and acute neurodegeneration
multiple sclerosis
Parkinson's disease
Down's syndrome
stroke
skull/brain trauma
migraine
O. Diseases of the kidneys:
nephrotic syndrome
haemodialysis
uraemia
P. Various toxicities:
OKT3 therapy
anti-CD3 therapy
cytokine therapy
chemotherapy
radiation therapy
chronic salicylate intoxication
Q. Metabolic/idiopathic diseases:
Wilson's disease
haemachromatosis
alpha-1-antitrypsin deficiency
diabetes
Hashimoto's thyroiditis
osteoporosis
hypothalamic pituitary adrenal axis evaluation
primary biliary cirrhosis In vitro investigations in plaque reduction tests using different viruses showed an inhibition of growth at substance concentrations of from 0.1 to 1000/µg/ml. The toxicity of the substances according to the invention is relatively low. They may be used in particular as effective preventative or therapeutic agents against influenza, AIDS or herpes diseases of the skin and mucous membranes. The daily dose for adults during the disease is of the order of about 5 to 1000 mg of active substance per day.

The compounds according to the invention may be administered by parental, subcutaneous, intravenous, intramuscular and intraperitoneal route. In this case, the carrier substance is a sterile liquid such as water or oil, the oil being of vegetable, animal or synthetic origin. Conventional glucose solutions are used as the injectable solutions. The liquid carriers for the injectable solutions generally contain 0.5 to 26% by weight of active substance. The compounds according to the invention may be administered orally with equal success. The compounds are also suitable for treating pneumonia and are administered in the form of a vapour or spray to the oral and nasal cavity. For oral administration, compositions in the form of tablets, capsules, powders, solutions, suspensions or elixirs are particularly preferred. The quantity of active ingredient in these preparations is at least 1% by weight, based on the total weight of the composition. The active substances according to the invention may also be administered topically, e.g. in ointments, creams, emulsions or lotions.

The Examples which follow show some possible formulations for the preparations:

FORMULATION EXAMPLES

1. Tablets
Composition:

| Active substance according to the invention | 20 parts by weight |
|---|---|
| Stearic acid | 6 parts by weight |
| Glucose | 474 parts by weight |

The ingredients are processed in the usual way to form tablets weighing 500 mg. If desired, the content of active substance may be increased or reduced and the quantity of glucose reduced or increased accordingly.

2. Suppositories
Composition:

| Active substance according to the invention | 100 parts by weight |
|---|---|
| Powdered lactose | 45 parts by weight |
| Cocoa butter | 1555 parts by weight |

The ingredients are processed in the usual way to form suppositories weighing 1.7 g.

3. Powder for Inhalation

Micronised powdered active substance (compound of formula I; particle size about 0.5 to 7 $\mu$m) is packed into hard gelatine capsules in a quantity of 5 mg, optionally with the addition of micronised lactose. The powder is inhaled from conventional inhalers, e.g. according to DE-A 33 45 722, to which reference is hereby made.

The compounds according to the invention can be prepared starting from compounds known from the prior art, using the processes described in the following Examples, inter alia. Other different embodiments of the invention and processes will be apparent to anyone skilled in the art from the present specification. However, it is expressly pointed out that these Examples and the associated specification are intended solely for purposes of explanation and should not be regarded as restricting the invention. Reference is further made to German Patent Application P 196 21 038.0 for additional information.

Example 1

Preparation of 1-(undecylideneamino)guanidine [C11AG]

1 mol (170.3 g) of undecanol, 1.1 mol (150 g) of aminoguanidine hydrogen carbonate and 1 g of p-toluenesulphonic acid are mixed with 500 ml of toluene and refluxed with stirring. As soon as 2 mol of water have been separated using the water separator, the mixture is allowed to cool, concentrated by rotary evaporation and the dark red oil is taken up in 250 ml of petroleum ether 40/60°. The precipitate formed is suction filtered and washed again with petroleum ether. For recrystallisation the precipitate is dissolved in ethyl acetate and mixed with petroleum ether at boiling temperature (boiling range 40 to 60° C.) until beginning to turn cloudy. Fine crystals are obtained, m.p. 101° C. The structure and purity of the compound were confirmed by analytical and spectroscopic data.

The other compounds mentioned in Example 3 are prepared analogously.

Example 2

Preparation of 1-(undecylamino) guanidine [$H_2$C11AG]

1.2 g of 1-(undecylideneamino)guanidine are placed in an autoclave and hydrogenated over a period of 12 hours in the presence of 0.1 g of 10% palladium on activated charcoal as hydrogenation catalyst in 20 ml of 100% acetic acid under a hydrogen pressure of 60 bar at ambient temperature. Then the catalyst is filtered off and the colourless solution is evaporated to dryness in vacuo.

In this way the title compound is isolated, after recrystallisation from ethyl acetate, in the form of colourless crystals melting in the range from 70–72° C. in quantitative yield.

Example 3

The virostatic properties were determined by in vitro tests. The following virus strains were used:
herpes virus
vesicular stomatitis virus
BVI 1

Cell cultures (monkey kidney cells or human fibroblasts) are infected with herpes and a series of cultures are exposed to medium containing various concentrations of the test substance. After 24 hours the concentration of the virus descendants in the cell culture supernatant is determined by plaque assays. The concentration of substance at which the virus replication is inhibited by 50% ($IC_{50}$) is determined from dosage/activity curves.

The results obtained from some substances by way of example are listed in the following Table.

| Substance | $IC_{50}$ $\mu M$ |
|---|---|
| 1 - (octylidene-amino) guanidine | 49.7 |
| 1 - (nonylidene-amino) guanidine | 29.0 |
| 1 - (decylidene-amino) guanidine | 28.9 |
| 1 - (undecylidene-amino) guanidine | 6.8 |
| 1 - (dodecylideneamino) guanidine | 3.2 |
| 1 - (anthracen-9-ylmethylene-amino) guanidine | 1.5 |
| 1 - (indol-3-ylmethylene-amino) guanidine | 19.8 |
| 1 - (phenalen-1-ylidene-amino) guanidine | 45.4 |

Example 4

Protection from endotoxic shock by C11AG is illustrated by FIG. 1:

Mice (strain NMRI/Nu, 8 weeks old, female) were each given 0.2 mg of endotoxin from *E. coli* (Sigma, Munich) by intraperitoneal route. The 10 control animals, who had been given 0.2 ml of 5% glucose subcutaneously, died within 24 hours. Nine animals were injected subcutaneously with 50 mg/kg of C11AG 30 minutes before the endotoxin treatment. Of this group, only 2 animals died.

Example 5
Inhibition of Collagen-induced Arthritis in the Mouse

An autoimmune reaction against cartilagenous tissue was produced by injecting collagen into DBA/I mice as described (Holmdahl, R. et al., Immunology, 65, 305–310, 1988). Groups of 10 animals were used as control or were given 50 mg/kg or 100 mg/kg of C11AG per day by oral route. The drug was administered in the food (Altromin, powdered food) and the dosage was calculated from the daily food intake. The symptoms were evaluated daily for each individual paw from 0.5–3 as described [R. Holmdahl, et al., Immunology, 65, 305–310, (1988)]. The total symptoms of every animal in each group—on day 7 after the booster injection—are shown in the following Table:

| Treatment | Total Symptoms |
| --- | --- |
| Control | 0 |
| Collagen | 35 |
| Collagen/50 mg/kg C11AG | 4.5 |
| Collagen/100 mg/kg C11AG | 1 |

20 days after the booster injection the animals were killed and the joints were examined by histopathology resulting in the following picture:

In all the untreated animals, inflammatory processes were found, but in the animals and controls treated with 50 and 100 mg/kg of C11AG, no such inflammatory processes could be detected.

The results obtained seven days after the booster injection are graphically shown in FIG. 2.

Example 6

| Inhibition of neutral SMase | |
| --- | --- |
| Compound | Neutral SMase $IC_{50}$ [$\mu$M] |
| Octylidene-aminoguanidine | 63 |
| Decylidene-aminoguanidine | 44 |
| Undecylidene-aminoguanidine | 8.2 |
| Dodecylidene-aminoguanidine | 5.8 |
| Anthracen-9-ylmethylene-aminoguanidine | 1.9 |
| Indol-3-ylmethylene-aminoguanidine | 5 |
| Phenalen-1-ylidene-aminoguanidine | 54 |

$^{14}$C sphingomyelin (10 $\mu$g/ml) was incubated with neutral SMase (membrane fraction isolated from mice brains, 10 $\mu$g of protein/mixture [according to S. Gatt, Biochem. Biophys. Res. Commun. 68, 235–241 (1976)] in the presence of various concentrations of the test substances (for 2 hours at 37° C. 20 mM Tris, 1 mM $MgCl_2$.pH 7.5). Then the samples were extracted with 5 times the volume of chloroform/methanol (1:1) and the content of radioactive phosphorylcholine in the aqueous phase was determined. The $IC_{50}$ was obtained from dosage/activity curves.

Example 7
Inhibition of NO-synthase Induction by C11AG in Macrophages

RAW cells (mouse macrophage line, origin: American Type Culture Collection) were treated with 10 ng/ml of endotoxin from *E. coli* (LPS) in the presence of different concentrations of C11AG. After 16 hours the nitrite content in the culture medium was measured using the method described [K. Tschaikowsky, M. Meisner, F. Schonhuber and E. Rugheimer, Br. J. Pharmacol. 113 (3): 664–8 (1994)].

Measured Values:

| C11AG concentration [$\mu$g/ml] | OD 540 nm |
| --- | --- |
| 0 | 0.122 |
| 0.5 | 0.091 |
| 1 | 0.075 |
| 2 | 0.054 |
| 3 | 0.05 |
| 4 | 0.038 |

The inhibition of NO-synthase induction is graphically shown in FIG. 3; the $NO_2$ concentration [OD measured at 540 nm] is plotted against the C11AG concentration [$\mu$g/ml] for 10 ng/ml of LPS.

Example 8

C11AG-$IC_{50}$ determination of acidic and neutral SMase $^{14}$C sphingomyelin (10 $\mu$g/ml) were incubated with neutral SMase (membrane fraction isolated from mouse brains, 10 $\mu$g protein/mixture, according to Gatt, S. Biochem. Biophys. Res. Commun. 68, 235–241, 1976) or with acidic SMase (microsome fraction from macrophage 5 $\mu$g of protein/mixture isolated according to Gatt, S. Biochem. Biophys. Res. Commun. 68, 235–241, 1976) in the presence of various concentrations of the test substances, for 2 hours at 37° C. in 20 mM Tris, 1 mM $MgCl_2$, pH 7.5 (neutral SMase) or in 50 mM sodium acetate, 1 mM $MgCl_{21}$ pH 5.6 (acid SMase). Then the samples were extracted with 5 times the volume of chloroform/methanol (1:1) and the content of radioactive phosphorylcholine in the aqueous phase was determined. The release of phosphorylcholine in the untreated mixtures corresponds to 100% enzyme activity.

Measured Values:

| C11AG concentration [$\mu$g/ml] | nSMase activity [%] | aSMase activity [%] |
| --- | --- | --- |
| 0 | 100 | 100 |
| 1 | 61 | 101 |
| 10 | 18 | 102 |
| 100 | 0 | 31 |

FIG. 4 shows, by a simple logarithmic representation, the sphingomyelinase inhibition for neutral and acidic sphingomyelinase [in %] as a function of the C11AG concentration [$\mu$g/ml].

Example 9
Inhibition of the Growth of Papillomas

*Mastomys natalensis* with papillomas triggered by a papilloma virus [see E. Amtmann and K. Wayss: ※ The *Mastomys natalensis* papilloma virus, in: P. Salzman and P. Howley (Eds.). The Papovaviridae, Vol. 2. Plenum Publishing Corporation (1987)] were given food containing various amounts of C11AG. The food consumption was measured and from this the daily oral dose of C11AG was calculated. The size of the papilloma was measured in two dimensions by means of a sliding gauge and the relative growth was calculated. 10 animals were treated per dose.

FIG. 5 graphically shows the average tumour size as a function of the duration of treatment for various doses of C11AG. Curve A shows the tumour growth of the control animals. Curve B shows the pattern of size for a dosage of 50 mg/kg C11AG and curve C shows the corresponding pattern for 100 mg/kg C11AG.

Example 10
Hydrogenated C11AG-IC$_{50}$: Measurement of Acidic and Neutral SMase $^{14}$C-sphingomyelin (10 μg/ml) was incubated with neutral SMase (membrane fraction from mouse brain, 10 μg of protein/batch, isolated according to Gatt, S. Biochem. Biophys. Res. Commun. 68, 235–241, 1976) or with acid SMase (microsome fraction from macrophages 5 μg of protein per batch [isolated according to S. Gatt, Biochem. Biophys. Res. Commun. 68, 235–241, (1976)] in the presence of various concentrations of the test substances for 2 hours at 37° C. in 20 mM Tris, 1 mM MgCl$_2$, pH 7.5 (neutral SMase) or in 50 mM sodium acetate, 1 mM MgCl$_2$, pH 5.6 (acidic SMase). Then the samples were extracted with 5 times the volume of chloroform/methanol (1:1) and the content of radioactive phosphorylcholine in the aqueous phase was determined. The release of phosphorylcholine in the untreated batches corresponds to 100%.

Measured Values:

| H$_2$C11AG concentration [μg/ml] | nSMase activity [%] | aSMase activity [%] |
|---|---|---|
| 0 | 100 | 100 |
| 1 | 73 | 100 |
| 10 | 22 | 97 |
| 100 | 2 | 32 |

FIG. 6 shows, by a simple logarithmic representation, the sphingomyelinase inhibition for neutral—curve A—and acidic sphingomyelinase [in %]—curve B—as a function of the H$_2$C11AG concentration [μg/ml].

Example 11
Prevention of Lethal Endotoxic Shock in the Mouse by H$_2$C$_{11}$AG 10 mice of the Balb C strain (about 8 weeks old) were given 0.7 mg of endotoxin from *E. coli* (in 0.2 ml of isotonic saline solution) by intraperitoneal injection. 10 animals were given 100 mg/kg of H$_2$C11AG (dissolved in twice distilled water) by oesphageal tube 2 hours before the LPS treatment. The control animals were given water. The surviving animals were observed for 12 days.

Results: control: 2 survivors (20%), 100 mg/kg H$_2$C11AG (hydrogenated C11AG): 9 survivors (90%).

FIG. 7 shows the survival rate of untreated experimental animals (A) compared with those who were treated with a dose of 100 mg H$_2$C11AG, as described above.

To illustrate the nomenclature used in the application, here are the structures of some of the compounds mentioned:

1-(Anthracen-9-ylmethylene-amino)guanidine

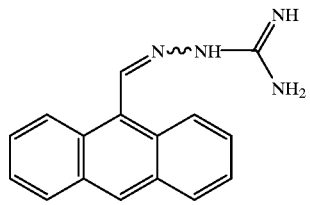

1-(Indol-3-ylmethylene-amino)guanidine

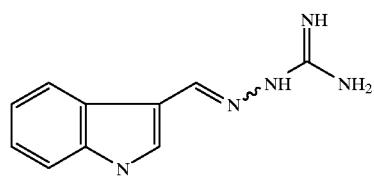

1-(Phenalen-1-ylidene-amino)guanidine

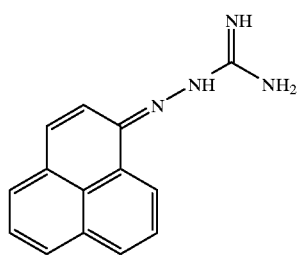

What is claimed is:
1. A compound having the formula:

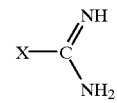

wherein X denotes —NH—NH—CH$_2$R$_1$ and R$_1$ denotes C$_8$ to C$_{20}$ -alkyl, either branched or unbranched; and optionally in the form of the individual optical isomers, mixtures of the individual isomers or racemates, tautomers and the corresponding acid addition salts with pharmaceutically acceptable acids.

2. A pharmaceutical composition comprising a compound of claim 1 with pharmaceutically acceptable acids together with pharmaceutically acceptable excipients and carriers.

3. A compound according to claim 1, wherein R$_1$ denotes an unbranched decyl group.

4. A compound according to claim 1 being 1-(undecylamino)guanidine.

5. A process for preparing a compound of the formula

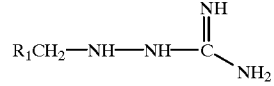

, wherein R$_1$ represents C$_8$ to C$_{20}$ alkyl, either branched or unbranched, said process comprising a first step of reacting an aldehyde having the general formula R$_1$CHO with an aminoguanidine, a second step of reducing the imine function resulting from the first step in the presence of a hydrogenation catalyst under elevated hydrogen pressure and isolating the reaction product, and optionally forming the corresponding acid addition salt with a pharmaceutically acceptable acid.

6. The compound of claim 1, in the form of a racemic mixture.

* * * * *